US010197482B2

(12) United States Patent
Gao et al.

(10) Patent No.: US 10,197,482 B2
(45) Date of Patent: Feb. 5, 2019

(54) METHOD AND SYSTEM FOR BENDING TEST OF FLEXIBLE SCREEN

(71) Applicants: Kunshan New Flat Panel Display Technology Center Co., Ltd., Kunshan, Jiangsu (CN); Kunshan Go-Visionox Opto-Electronics Co., Ltd., Kunshan, Jiangsu (CN)

(72) Inventors: Sheng Gao, Jiangsu (CN); Dongdong Liu, Jiangsu (CN); Xiuqi Huang, Jiangsu (CN)

(73) Assignees: Kunshan New Flat Panel Display Technology Center Co., Ltd., Kunshan (CN); Kunshan Go-Visionox Opto-Electronics Co., Ltd., Kunshan (CN)

( * ) Notice: Subject to any disclaimer, the term of this patent is extended or adjusted under 35 U.S.C. 154(b) by 0 days.

(21) Appl. No.: 15/105,981

(22) PCT Filed: Dec. 17, 2014

(86) PCT No.: PCT/CN2014/094111
§ 371 (c)(1),
(2) Date: Jun. 17, 2016

(87) PCT Pub. No.: WO2015/090206
PCT Pub. Date: Jun. 25, 2015

(65) Prior Publication Data
US 2017/0102302 A1  Apr. 13, 2017

(30) Foreign Application Priority Data
Dec. 18, 2013 (CN) .......................... 2013 1 0698708

(51) Int. Cl.
*G01N 3/00* (2006.01)
*G01N 3/20* (2006.01)
(Continued)

(52) U.S. Cl.
CPC ................ *G01N 3/20* (2013.01); *G01N 3/00* (2013.01); *G09G 3/006* (2013.01);
(Continued)

(58) Field of Classification Search
CPC ... G01N 2203/0282; G01N 2203/0023; G01N 2203/0067; G01N 2203/0005;
(Continued)

(56) References Cited

U.S. PATENT DOCUMENTS 5,616,848 A * 4/1997 Hemingway ............ G01N 3/20
73/838
8,461,860 B2 * 6/2013 Kim ...................... G01M 5/005
324/762.01
(Continued)

FOREIGN PATENT DOCUMENTS

CN     1587967       3/2005
CN     2837820 Y    11/2006
(Continued)

OTHER PUBLICATIONS

International Search Report and Written Opinion, dated Mar. 17, 2015, in corresponding International Patent Application No. PCT/CN2014/094111.
(Continued)

*Primary Examiner* — Jonathan M Dunlap
(74) *Attorney, Agent, or Firm* — Maier & Maier, PLLC

(57) ABSTRACT

A method for bending test of a flexible screen is disclosed, including: connecting the flexible screen to a mounting device; conducting a mechanical extrusion test to the flexible screen to bend the flexible screen, in which an extrusion point for the mechanical extrusion test is away from connection points between the flexible screen and the mounting device; and conducting a bending performance detection to the flexible screen. And a system for bending test of a
(Continued)

flexible screen is also disclosed. The bending performance of the flexible screen can be tested by simulating an environment for the flexible screen in the mechanical extrusion test, and compared with the traditional methods and apparatuses for bending test of a flexible screen, the method and system for bending test of a flexible screen according to the present disclosure are convenience for operation and low cost in testing.

15 Claims, 2 Drawing Sheets

(51) Int. Cl.
  *H01L 51/00*  (2006.01)
  *G09G 3/00*  (2006.01)
  *G01N 33/00*  (2006.01)
  *H01L 51/56*  (2006.01)

(52) U.S. Cl.
  CPC ...... *H01L 51/0031* (2013.01); *H01L 51/0097* (2013.01); *G01N 2033/0078* (2013.01); *G01N 2203/0282* (2013.01); *H01L 51/56* (2013.01); *Y02E 10/549* (2013.01)

(58) Field of Classification Search
  CPC ... G01N 2203/0003; G01N 2203/0037; G01N 2203/0278; G01N 2203/0641; G01N 3/20; G01N 19/08
  USPC .......................... 73/849–854, 760, 800, 812
  See application file for complete search history.

(56) References Cited

U.S. PATENT DOCUMENTS

| | | | |
|---|---|---|---|
| 8,943,898 B2* | 2/2015 | Bell | G02F 1/1309 73/856 |
| 2003/0061885 A1 | 4/2003 | Auch et al. | |
| 2006/0137465 A1* | 6/2006 | Lee | G01N 3/20 73/794 |
| 2007/0193364 A1* | 8/2007 | Wong | G01N 3/20 73/849 |
| 2008/0083288 A1* | 4/2008 | Glaesemann | G01N 3/20 73/849 |
| 2008/0229844 A1* | 9/2008 | MacKey | G01M 5/0033 73/852 |
| 2009/0272198 A1* | 11/2009 | Wen | G01N 3/20 73/849 |
| 2012/0022802 A1* | 1/2012 | Sakuma | G01N 3/42 702/43 |
| 2012/0067134 A1* | 3/2012 | Bell | G02F 1/133305 73/800 |
| 2012/0285257 A1 | 11/2012 | Kim | |
| 2013/0327152 A1* | 12/2013 | Chen | G01N 3/08 73/818 |
| 2014/0174195 A1* | 6/2014 | Shen | G01N 3/20 73/851 |
| 2014/0238145 A1* | 8/2014 | Tran | G01N 3/20 73/851 |
| 2015/0033870 A1* | 2/2015 | Lee | G01N 3/20 73/849 |
| 2016/0103048 A1* | 4/2016 | Okazaki | G01N 3/20 73/853 |
| 2016/0282249 A1* | 9/2016 | Leroux | G01N 3/42 |
| 2016/0334315 A1* | 11/2016 | Leroux | G01N 3/40 |

FOREIGN PATENT DOCUMENTS

| | | |
|---|---|---|
| CN | 1963428 A | 5/2007 |
| CN | 101324524 A | 12/2008 |
| CN | 101788427 A | 7/2010 |
| CN | 101793651 A | 8/2010 |
| CN | 103149044 A | 6/2013 |
| CN | 203811355 U | 9/2014 |
| JP | H07210636 A | 8/1995 |
| JP | H08136427 A | 5/1996 |
| JP | 2002062231 A | 2/2002 |
| JP | 2005091187 A | 4/2005 |
| JP | 2005241434 A | 9/2005 |
| KR | 20100026366 A | 3/2010 |
| KR | 20120010801 A | 2/2012 |
| KR | 20130111786 A | 10/2013 |
| TW | 200916748 A | 4/2009 |
| TW | 201326796 A | 7/2013 |

OTHER PUBLICATIONS

European Search Report and Written Opinion, dated Aug. 4, 2017, in corresponding European Patent Application No. 14872266.3.
Japanese First Office Action, dated Jun. 6, 2017, in corresponding Japanese Patent Application No. 2016-541302.
Japanese Second Office Action, dated Oct. 17, 2017, in corresponding Japanese Patent Application No. 2016-541302.
Taiwan Office Action, dated Dec. 21, 2015, in corresponding Taiwan Patent Application No. 103144248.
Korean Office Action, dated Dec. 12, 2017, in corresponding Korean Patent Application No. 10-2016-7019015.
Chinese Search Report and First Office Action, dated Nov. 2, 2016, in corresponding Priority Chinese Patent Application No. 201310698708.4.
Chinese Supplementary Search Report and Second Office Action, dated Jun. 28, 2017, in corresponding Chinese Patent Application No. 201310698708.4.

\* cited by examiner

METHOD AND SYSTEM FOR BENDING TEST OF FLEXIBLE SCREEN

CROSS REFERENCE TO RELATED APPLICATIONS

This application is a national phase application based on PCT/CN2014/094111, filed Dec. 17, 2014, which claims the priority of Chinese Patent Application No. 201310698708.4, filed Dec. 18, 2013, the contents of both of which are incorporated herein by reference.

FIELD

The present disclosure relates generally to the technical filed of flexible device test, and more particularly, to a method and a system for bending test of a flexible screen.

BACKGROUND

A flexible display is a deformable and flexible display unit, made of a soft material. The flexible display can be as thin as paper, and even if the power is cut off, the content in the display will not disappear, so the flexible display is also referred to as "electronic paper". Because of the characteristics of being extremely light and thin, having low power consumption and being deformable, the flexible display is already widely used in portable electronic devices. The bending performance of the flexible screen of the flexible display directly affects the quality of the flexible display, so it is necessary to make an evaluation on the bending performance of the flexible screen.

A drum-type bending device is always used in traditional methods and devices for bending test of flexible screen to mechanically bend the flexible screen. Specifically, a number of drums of a same curvature or different curvatures can be used to transmit the flexible screen to bend the flexible screen, and the flexible screen can be conducted in a mechanical reliability test. If only one drum is used to transmit the flexible screen, a relative unit is required to press the flexible screen to bend the flexible screen; and if a plurality of drums are used to transmit the flexible screen, a drawing device is required to draw the flexible screen so that the flexible screen can be normally transmitted on the plurality of drums. Using a drum or a plurality of drums to transmit and bend the flexible screen has disadvantages of complexity of operation and high-cost of testing.

SUMMARY

In view of the above, there is a need to provide to a method and a system for bending test of a flexible screen, which are convenience for operation and low cost in testing.

According to an aspect of the present disclosure, a method for bending test of a flexible screen is provided, including:
connecting the flexible screen to a mounting device;
conducting a mechanical extrusion test to the flexible screen to bend the flexible screen by placing an extrusion point for the mechanical extrusion test away from connection points between the flexible screen and the mounting device; and
conducting a bending performance detection to the flexible screen.

In one embodiment, the flexible screen is a polygonal flexible screen, and the connecting the flexible screen to a mounting device includes connecting opposite ends of the flexible screen to the mounting device; and
conducting a mechanical extrusion test to the flexible screen includes approaching, by the extrusion device, the flexible screen, and extruding the flexible screen so that the degree of bending of the flexible screen is gradually increased.

In one embodiment, the conducting a mechanical extrusion test to the flexible screen includes extruding the flexible screen by a preset force at a preset frequency within a preset time period.

In one embodiment, there are a plurality of preset frequencies and a plurality of preset forces, and the conducting a mechanical extrusion test to the flexible screen includes extruding the flexible screen by at least one preset force respectively at one preset frequency.

In one embodiment, the conducting a mechanical extrusion test to the flexible screen includes mechanically extruding a plurality of preset extrusion points in the flexible screen respectively.

In one embodiment, the conducting a mechanical extrusion test to the flexible screen includes mechanically extruding the flexible screen by a plurality of preset extrusion areas.

In one embodiment, conducting a bending performance detection to the flexible screen includes:
detecting a mechanical reliability of the flexible screen after conducting the mechanical extrusion test to the flexible screen.

In one embodiment, conducting a bending performance detection to the flexible screen includes:
detecting the optical reliability and/or electrical reliability of the flexible screen at the time of/after conducting the mechanical extrusion test to the flexible screen.

According to another aspect of the present disclosure, a system for bending test of a flexible screen is provided, including:
a mounting device, configured to connected with the flexible screen;
an extrusion device, configured to conduct a mechanical extrusion test to the flexible screen to bend the flexible screen by placing an extrusion point for the mechanical extrusion test away from connection points between the flexible screen and the mounting device; and
a detection device, configured to conduct a bending performance detection to the flexible screen.

In one embodiment, the mounting device is adapted to be connected to opposite ends of the flexible screen; the extrusion device is adapted to approach the flexible screen, and extrude the flexible screen so that the degree of bending of the flexible screen is gradually increased.

In one embodiment, the mounting device includes a fixing support, and a mounting component provided on the fixing support and configured to fix the flexible screen.

In one embodiment, the mounting component is made of an elastic material and is adapted to be deformed and stretched when the flexible screen is extruded.

In one embodiment, the extrusion device includes an extrusion component and a drive, in which the extrusion component includes a connecting rod and an extrusion head connected with the connecting rod; and the drive is fixed on the fixing support, the connecting rod is connected to the extrusion head, and the extrusion head is driven to conduct the mechanical extrusion test to the flexible screen.

In one embodiment, the mounting device further includes a regulating device provided on the fixing support and adapted to move with respect to the fixing support, the drive being connected to the fixing support via the regulating device.

In one embodiment, the surface of the extrusion head is a smoothly curved surface.

In one embodiment, the connecting rod is coupled to the extrusion head in a threaded connection.

In the above method and system for bending test of a flexible screen, the flexible screen is connected to a mounting device to conduct a mechanical extrusion test to the flexible screen to bend the flexible screen, in which an extrusion point for the mechanical extrusion test is away from connection points between the flexible screen and the mounting device, and bending performance detection is conducted to the flexible screen. The bending performance of the flexible screen can be tested by simulating an environment for the flexible screen in the mechanical extrusion test. Compared with the traditional methods and apparatuses for bending test of a flexible screen, the method and system for bending test of a flexible screen according to the present disclosure are convenience for operation and low cost in testing.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE PREFERRED EMBODIMENTS

In the following description of embodiments, reference is made to the accompanying drawings which form a part hereof, and in which it is shown by way of illustration specific embodiments of the disclosure that can be practiced. It is to be understood that other embodiments can be used and structural changes can be made without departing from the scope of the disclosed embodiments.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Figure 1:
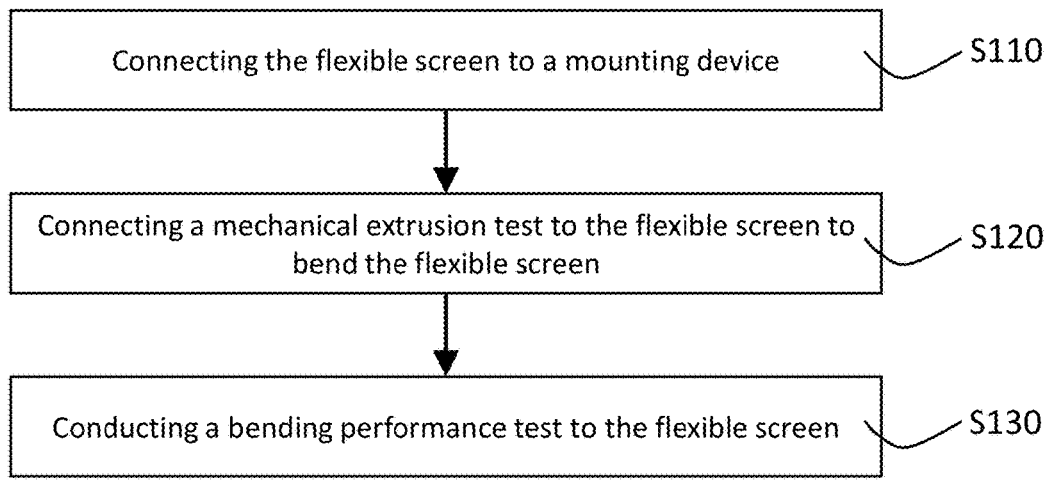
FIG. 1 is a flow diagram illustrating a method for bending test of a flexible screen according to one embodiment of the present disclosure.

As shown in FIG. 1, a method for bending test of a flexible screen includes:

step S110, connecting the flexible screen to a mounting device;

The mounting device may fix the flexible screen in a relative flexible manner that when the flexible screen is extruded, the mounting device can be deformed so that the flexible screen can be bent normally. In the embodiment, the mounting device may fix the flexible screen in a relative flexible manner, so it can avoid that the force applied on the flexible screen is too heavy that the flexible screen may be broken when conducting a mechanical extrusion test to the flexible screen. It will be appreciated that the mounting device may fix the flexible screen in a rigid manner in other embodiments that the mounting device cannot be deformed. If the mounting device fixes the flexible screen in a rigid manner, the force for extrusion should be controlled when conducting a mechanical extrusion test.

In one embodiment, the step S110 includes connecting opposite ends of the flexible screen to the mounting device. The flexible screen may be quadrangular or pentagonal. When conducting a mechanical extrusion test to the flexible screen the fixation effect of the flexible screen can be ensured by fixing the connection between the opposite ends of the flexible screen and the mounting device. It will be appreciated that if two adjacent ends of the flexible screen are connected to the mounting device, at least one of the other ends of the flexible screen should be connected to the mounting device to ensure the fixation effect. That is, in the embodiment, reducing the number of connection points between the mounting device and the flexible screen can simplify the structure of the mounting device and reduce the testing cost, under the precondition of ensuring the fixation effect of the flexible screen.

Further, when the flexible screen is in a symmetrical shape, such as rectangle, diamond or regular pentagon, the two connection points between the flexible screen and the mounting device locate on a symmetric axis of the flexible screen. For example, if the flexible screen is in a shape of rectangle, the two connection points are on the middle of the opposite sides of the flexible screen respectively. And if the flexible screen is in a shape of regular pentagon, the two connection points are on the middle of one side of the flexible screen and a vertex of the flexible screen opposite to the side of the flexible screen respectively. The connection points locate on the symmetric axis of the flexible screen, so that a same pulling force applied on the positions of the two connection points of the mounting device can be ensured as the flexible screen being bent when conducting a mechanical extrusion test to the flexible screen, and it can avoid the flexible screen falls off caused by the pulling force applied on the position of one of the connection points of the mounting device is too heavy, to improve the testing stability.

step S120, conducting a mechanical extrusion test to the flexible screen to bend the flexible screen;

The extrusion point for the mechanical extrusion test is away from the connection points between the flexible screen and the mounting device, that is, the extrusion point and the connection point are not on the same point. Conducting a mechanical extrusion test to the flexible screen to bend the flexible screen can simulate a practical application environment of the flexible screen. Specifically, the extrusion device can approach the flexible screen, and extrude the flexible screen so that the degree of bending of the flexible screen is gradually increased.

In one embodiment, the flexible screen is in a symmetrical shape, the two connection points between the flexible screen and the mounting device are on a symmetric axis of the flexible screen. Further, the extrusion point for the mechanical extrusion test may be on a connecting line between the two connection points. Because the connecting line between the two connection points is the symmetric axis of the flexible screen, when conducting a mechanical extrusion test to the flexible screen a smaller extrusion force can have a better extrusion effect, compared with the case that the extrusion point is not on the connecting line between the two connection points. It thus can further reduce the testing cost.

In one embodiment, the conducting a mechanical extrusion test to the flexible screen includes extruding the flexible screen by a preset force at a preset frequency within a preset time. The preset frequency may be 30 times per minute, and the preset force may be 50 Newtons. The preset frequency and the preset force corresponding to a flexible screen 300 of a different size and structure can be adjusted according to need. In the embodiment, the flexible screen is subjected to multiple mechanical extrusions in a preset time, which can better conform to the practical application environment of the flexible screen, and improve the accuracy of the test. A controller may be used to control a motor to drive an extrusion device to extrude the flexible screen based on the preset frequency and preset force. The preset frequency is an extrusion frequency of the extrusion device, the preset force is an extrusion force of the extrusion device, and the preset frequency, preset force and the preset time can be adjusted based on the circumstances. The motor can be connected to the extrusion device via an expansion link. The extrusion force of the extrusion device can be controlled by changing the expansion length of the expansion link with the motor.

Further, there may be a plurality of preset frequencies and a plurality of preset forces. The conducting a mechanical extrusion test to the flexible screen includes extruding the flexible screen by at least one preset force respectively at one preset frequency. One preset frequency may correspond to one preset force, or all or part of the preset frequencies correspond to the plurality of preset forces. For example, the preset frequencies includes a frequency A, a frequency B and a frequency C, the preset force includes a force A, a force B and a force C, and if all of the preset frequencies correspond to the plurality of preset forces, the flexible screen may be extruded by at least two of the force A, force B and force C at the frequency A, and it is similar at the frequency B or C. Extruding the flexible screen by a different force and at a different frequency can further conform to the practical application environment of the flexible screen, and improve the accuracy of the test.

In one embodiment, the conducting a mechanical extrusion test to the flexible screen includes mechanically extruding a plurality of preset extrusion points in the flexible screen respectively. In the embodiment, conducting a multipoint extrusion test to the flexible screen can better conform to the practical application environment of the flexible screen, and improve the accuracy of the test.

In addition, the conducting a mechanical extrusion test to the flexible screen includes mechanically extruding the flexible screen by a plurality of preset extrusion areas. Specifically, the extrusion area may be adjusted by changing the volume of the extrusion device, and the flexible screen can be mechanically extruded by a different extrusion area, which also better conforms to the practical application environment of the flexible screen, and further improves the accuracy of the test.

In one embodiment, the mechanical extrusion test includes: conducting a multipoint extrusion to the flexible screen by an extrusion area, that is, mechanically extruding the plurality of extrusion points of the flexible screen respectively by a different force at a different frequency for a set time; and changing the extrusion device, and conducting a further multipoint extrusion to the flexible screen by another extrusion area.

step S130, conducting a bending performance detection to the flexible screen.

In one embodiment, the step S130 may include detecting the mechanical reliability of the flexible screen after conducting the mechanical extrusion test to the flexible screen.

The detecting the mechanical reliability of the flexible screen is detecting the extent of the damage at the flexible screen after the mechanical extrusion test. Specifically, the flexible screen may be scanned and detected by a scanner, and the flexible screen can be classified, for example, to good products, qualified products and defective products, according to the extent of the damage after getting the detection results. Then the flexible screen can be tagged with a level of its mechanical reliability.

In one embodiment, the step S130 also includes detecting the optical reliability and/or electrical reliability of the flexible screen when conducting the mechanical extrusion test to the flexible screen or after conducting the mechanical extrusion test to the flexible screen.

For example, in one embodiment that the optical reliability and the electrical reliability are detected, the optical reliability is detected by detecting the light transmittance of the flexible screen by irradiating the flexible screen with a light source, and the electrical reliability is detected by detecting the electrical parameter of the semiconductor device in the flexible screen, specifically, including using a semiconductor parameter tester to connect the semiconductor device in the flexible screen, conducting an electrical parameter test, and evaluating the change of the electrical parameter before and after bending.

That is, the bending performance detection to the flexible screen in the step S130 can be one or more of the detections of the mechanical reliability, the optical reliability and the electrical reliability of the flexible screen.

The above method for bending test of a flexible screen connects the flexible screen to a mounting device, conducts a mechanical extrusion test to the flexible screen to bend the flexible screen, in which an extrusion point for the mechanical extrusion test is away from connection points between the flexible screen and the mounting device, and conducts a bending performance detection to the flexible screen. The bending performance of the flexible screen can be tested by simulating an environment for the flexible screen in the mechanical extrusion test, and compared with the traditional methods for bending test of a flexible screen, the method for bending test of a flexible screen according to the present disclosure is convenience for operation and low cost in testing.

Figure 2:
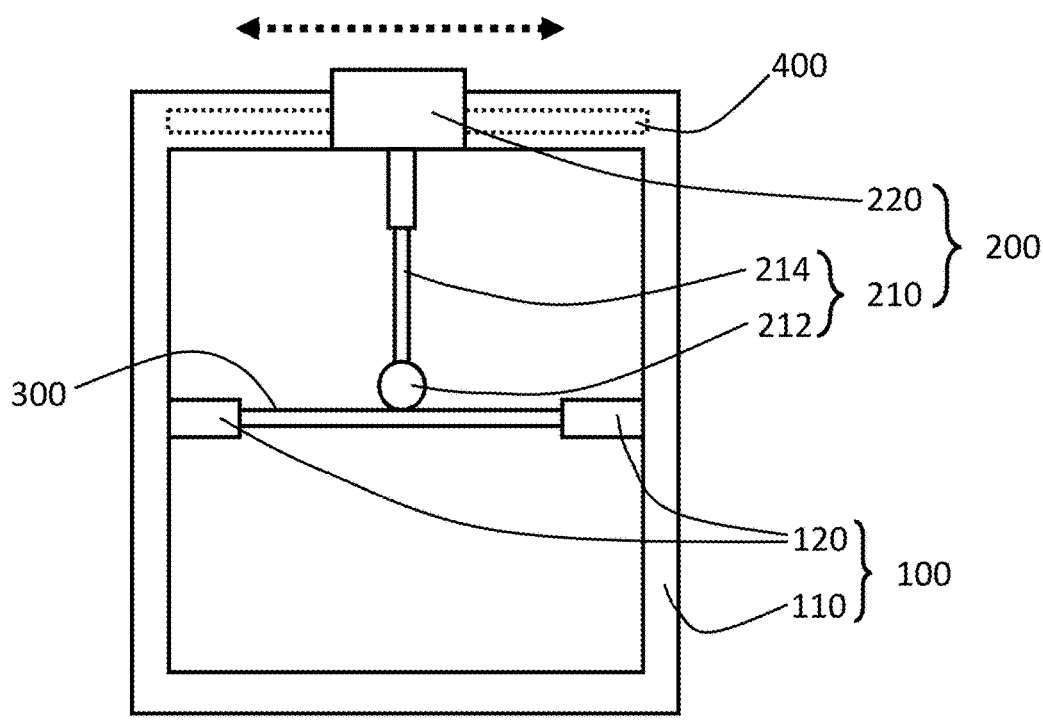
FIG. 2 is a schematic diagram illustrating a system for bending test of a flexible screen before a mechanical extrusion test according to one embodiment of the present disclosure.
Figure 3:
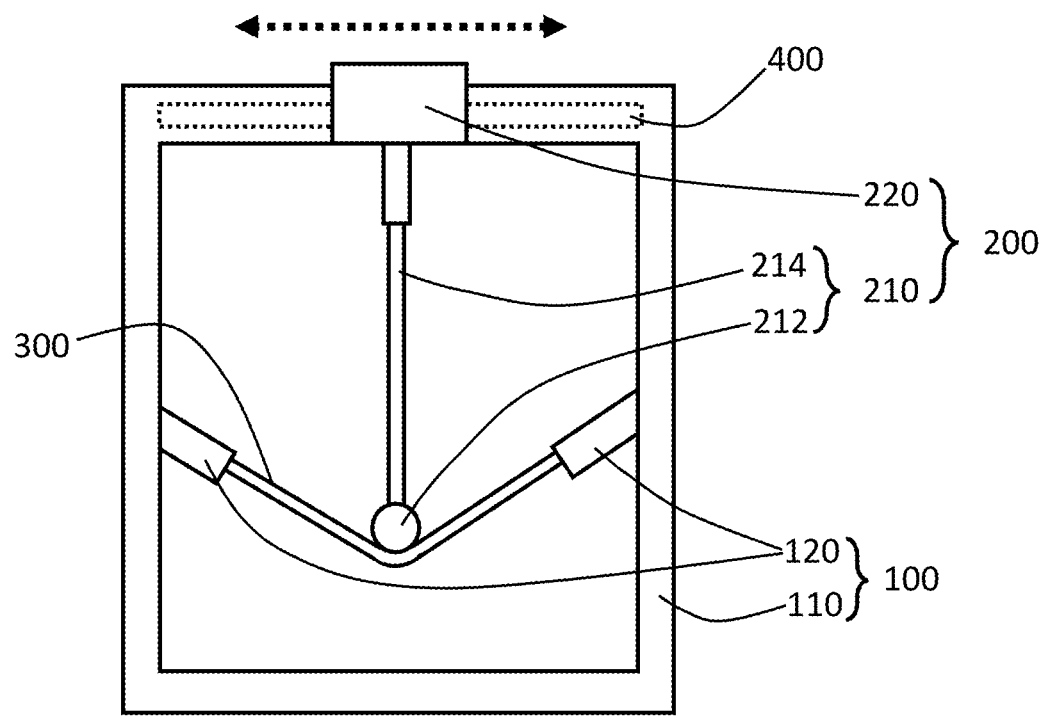
FIG. 3 is a schematic diagram illustrating a system for bending test of a flexible screen in a mechanical extrusion test according to one embodiment of the present disclosure.

In addition, a system for bending test of a flexible screen is also provided. As shown in FIG. 2 and FIG. 3, the system for bending test of a flexible screen includes a mounting device 100, an extrusion device 200 and a detection device (not shown).

The mounting device 100 is configured to be connected to the flexible screen 300.

The mounting device 100 may fix the flexible screen 300 in a relative flexible manner that when the flexible screen 300 is extruded, the mounting device 100 can be deformed so that the flexible screen 300 can be bent normally.

In one embodiment, the mounting device 100 is connected to opposite ends of the flexible screen 300. The flexible screen 300 may be quadrangular or pentagonal. When conducting a mechanical extrusion test to the flexible screen 300 the fixation effect of the flexible screen 300 can be ensured by fixing the connection between the opposite ends of the flexible screen and the mounting device. That is, in the embodiment, reducing the number of connection points between the mounting device 100 and the flexible screen 300 can simplify the structure of the mounting device 100 and reduce the testing cost, under the precondition of ensuring the fixation effect of the flexible screen 300.

Further, when the flexible screen 300 is in a symmetrical shape, such as rectangle, diamond or regular pentagon, the two connection points between the flexible screen 300 and the mounting device 100 locate on a symmetric axis of the flexible screen 300. A same pulling force applied on the positions of the two connection points of the mounting device 100 can be ensured as the flexible screen 300 being bent when conducting a mechanical extrusion test to the flexible screen 300, and it can avoid the flexible screen 300 falls off caused by the pulling force applied on the position of one of the connection points of the mounting device 100 is too heavy, to improve the testing stability.

In one embodiment, the mounting device 100 includes a fixing support 110, and a mounting component 120 provided on the fixing support 110 and configured to relatively fix the flexible screen 300.

In the embodiment, the fixing support 110 can be a hollow box or a similar mechanism. The mounting component 120 can be deformed and stretched when the flexible screen 300 is extruded, and specifically, the mounting component 120 can be a stainless steel spring or be made of a retractable elastic material. The mounting device 100 may fix the flexible screen 300 in a relative flexible manner, so it can avoid that the force applied on the flexible screen 300 is too heavy that the flexible screen 300 may be broken when conducting a mechanical extrusion test to the flexible screen 300. It will be appreciated that the concrete structures of the fixing support 110 and the mounting component 120 are respectively not the only one In other embodiments, the mounting device 100 may fix the flexible screen 300 in a rigid manner that the mounting device 100 cannot be deformed. If the mounting device 100 fixes the flexible screen in a rigid manner, the force for extrusion should be controlled when conducting a mechanical extrusion test.

The extrusion device 200 is configured to conduct a mechanical extrusion test to the flexible screen 300 to bend the flexible screen 300.

The extrusion point for the mechanical extrusion test is away from the connection points between the flexible screen 300 and the mounting device 100, that is, the extrusion point and the connection point are not on the same point. Conducting a mechanical extrusion test to the flexible screen 300 to bend the flexible screen 300 can simulate a practical application environment of the flexible screen 300. Specifically, the extrusion device 200 can approach the flexible screen 300, and extrude the flexible screen 300 so that the degree of bending of the flexible screen 300 is gradually increased.

In one embodiment, the flexible screen 300 is in a symmetrical shape, the two connection points between the flexible screen 300 and the mounting device 100 are on a symmetric axis of the flexible screen 300. Further, the extrusion point for the mechanical extrusion test may be on a connecting line between the two connection points. Because the connecting line between the two connection points is the symmetric axis of the flexible screen 300, when conducting a mechanical extrusion test to the flexible screen 300 a smaller extrusion force can have a better extrusion effect, compared with the case that the extrusion point is not on the connecting line between the two connection points. It thus can further reduce the testing cost.

The extrusion device 200 can include an extrusion component 210 and a drive 220.

The extrusion component 210 includes an extrusion head 212 and a connecting rod 214, and the extrusion head 212 is connected with the connecting rod 214. The surface of the extrusion head 212 is a smoothly curved surface, which can avoid the interference to the test caused by the flexible screen being cut by the extrusion head 212 when conducting a mechanical extrusion test, to improve the accuracy of the test. Specifically, the extrusion head 212 is in a shape of sphere in the embodiment.

The extrusion head 212 can be coupled to the connecting rod 214 in a threaded connection, so that it is convenient to replace extrusion head 212 of different volumes. In mechanical extrusion test to the flexible screen 300, the flexible screen 300 can be mechanically extruded by a plurality of preset extrusion areas. Mechanically extruding the flexible screen 300 by different extrusion areas can better conform to the practical application environment of the flexible screen 300, and further improve the accuracy of the test.

The drive 220 is fixed on the fixing support 110, connected to the extrusion head 212 via the connecting rod 214, and configured to drive the extrusion head 212 to conduct a mechanical extrusion test to the flexible screen 300. The drive 220 includes a controller and a motor. The controller controls the motor to drive the extrusion head 212 to extrude the flexible screen 300. In the embodiment, the flexible screen 300 is fixed in a horizontal direction, and the drive 220 is positioned above the flexible screen 300. It will be appreciated that the fixed position of the drive 220 on the fixing support 110 may differ according to the fixed direction of the flexible screen 300.

In one embodiment, the drive 220 may drive the extrusion head 212 to extrude the flexible screen 300 by a preset force at a preset frequency within a preset time. The preset frequency may be 30 times per minute, and the preset force may be 50 Newtons. The preset frequency and the preset force corresponding to a flexible screen 300 of a different size and structure can be adjusted according to need. In the embodiment, the flexible screen 300 is subjected to multiple mechanical extrusions in a preset time, which can better conform to the practical application environment of the flexible screen, and improve the accuracy of the test. The preset frequency is an extrusion frequency of the extrusion head 212, the preset force is an extrusion force of the extrusion head 212, and the preset frequency, preset force and the preset time can be adjusted based on the circumstances. The drive 220 can be connected to the connecting rod 214 via an expansion link. The extrusion force of the extrusion head 212 can be controlled by changing the expansion length of the expansion link with the drive 220.

Further, there may be a plurality of preset frequencies and a plurality of preset forces. The drive 220 may drive the extrusion head 212 to extrude the flexible screen 300 by at least one preset force at one preset frequency. That is, the flexible screen 300 can be extruded by a different force at a different frequency when conducting a mechanical extrusion test. One preset frequency may correspond to one preset force, or all or part of the preset frequencies correspond to the plurality of preset forces. For example, the preset frequencies includes a frequency A, a frequency B and a frequency C, the preset force includes a force A, a force B and a force C, and if all of the preset frequencies correspond to the plurality of preset forces, the flexible screen may be extruded by at least two of the force A, force B and force C at the frequency A, and it is similar at the frequency B or C. Extruding the flexible screen 300 by a different force and at a different frequency can further conform to the practical application environment of the flexible screen 300, and improve the accuracy of the test.

In one embodiment, the mounting device 100 also includes a regulating device 400 provided on the fixing support 110 and adapted to move with respect to the fixing support 110. The drive 220 is connected to the fixing support 110 via the regulating device 400. In the embodiment, the position of the drive 220 can be moved by the regulating device 400 for mechanical extrusion for a number of set extrusion points on the flexible screen 300. Conducting a multipoint extrusion test to the flexible screen 300 can better conform to the practical application environment of the flexible screen 300, and improve the accuracy of the test.

In one embodiment, the mechanical extrusion test includes changing the position of the drive 220 by the regulating device 400; using the extrusion head 212 to conduct a multipoint extrusion to the flexible screen 300, that is, mechanically extruding the plurality of extrusion points of the flexible screen 300 respectively by a different force at a different frequency for a set time; and changing the extrusion head 212, and conducting a further multipoint extrusion to the flexible screen 300.

The detection device is configured to conduct a bending performance detection to the flexible screen 300.

The bending performance detection to the flexible screen 300 with the detection device can be one or more of the detections of the mechanical reliability, the optical reliability and the electrical reliability of the flexible screen 300. For example, in one embodiment that the bending performance detection includes the mechanical reliability, the optical reliability and the electrical reliability, the detection devices can include a scanner, an optical detector and an electrical detector.

The scanner is configured to scan the flexible screen 300 and detect the extent of the damage at the flexible screen 300 after the mechanical extrusion test. The flexible screen 300 can be classified, for example, to good products, qualified products and defective products, according to the extent of the damage after getting the detection results. Then the flexible screen 300 can be tagged with a level of its mechanical reliability.

The optical detector is configured to conduct an optical reliability test and detect the light transmittance of the flexible screen 300 in the mechanical extrusion test or after the mechanical extrusion test. The optical detector may include a light source part and a detection part respectively arranged on two sides of the flexible screen 300. The light signal form the light source part can irradiate the flexible screen 300, and the detection part can receive the light signal that passes through the flexible screen 300 to detect the light transmittance of the flexible screen.

The electrical detector is configured to conduct an electrical reliability test and detect the electrical parameter of the semiconductor device in the flexible screen 300 in the mechanical extrusion test or after the mechanical extrusion test. The electrical detector can be a semiconductor parameter tester which can be connected to the semiconductor device in the flexible screen for the electrical parameter test to evaluate the change of the electrical parameter before and after bending.

The above system for bending test of a flexible screen connects mounting device 100 to the flexible screen 300, conducts a mechanical extrusion test to the flexible screen 300 to bend the flexible screen 300 with the extrusion device 200, in which an extrusion point for the mechanical extrusion test is away from connection points between the flexible screen 300 and the mounting device 100, and conducts a bending performance test to the flexible screen 300 with the detection device. The bending performance of the flexible screen 300 can be tested by simulating an environment for the flexible screen 300 in the mechanical extrusion test, and compared with the traditional methods for bending test of a flexible screen, the system for bending test of a flexible screen according to the present disclosure is convenience for operation and low cost in testing.

The above are preferred embodiments of the invention described in detail, and should not be deemed as limitations to the scope of the present invention. It should be noted that variations and improvements will become apparent to those skilled in the art to which the present invention pertains without departing from its spirit and scope. Therefore, the scope of the present disclosure is defined by the appended claims.

The invention claimed is:

1. A method for bending test of a flexible screen, comprising:
    connecting the flexible screen to a mounting device, the mounting device adapted to fasten the flexible screen in a relative flexible manner using an elastic material so that the mounting device is deformed when the flexible screen is extruded;
    conducting a mechanical extrusion test to the flexible screen to bend the flexible screen by placing an extrusion point for the mechanical extrusion test away from connection points between the flexible screen and the mounting device; and
    conducting a bending performance detection to the flexible screen,
    wherein conducting a mechanical extrusion test includes approaching, by an extrusion device, to the flexible screen, the extrusion device including an extrusion head in a shape of sphere with a smoothly curved surface,
    wherein the extrusion head is regulated by a regulating device of the mounting device so that different positions of the extrusion point are selected in each test, and
    wherein the mechanical extrusion test is repeated up to multiple times in a preset time.

2. The method of claim 1, wherein the connecting the flexible screen to a mounting device comprises connecting opposite ends of the flexible screen to the mounting device; and conducting a mechanical extrusion test to the flexible screen comprises extruding the flexible screen so that the degree of bending of the flexible screen is gradually increased.

3. The method of claim 1, wherein the conducting a mechanical extrusion test to the flexible screen comprises extruding the flexible screen by a preset force at a preset frequency within a preset time period.

4. The method of claim 3, wherein there are a plurality of preset frequencies and a plurality of preset forces, and the conducting a mechanical extrusion test to the flexible screen comprises extruding the flexible screen by at least one preset force respectively at one preset frequency.

5. The method of claim 1, wherein the conducting a mechanical extrusion test to the flexible screen comprises mechanically extruding a plurality of preset extrusion points in the flexible screen respectively.

6. The method of claim 1, wherein the conducting a mechanical extrusion test to the flexible screen comprises mechanically extruding the flexible screen by a plurality of preset extrusion areas.

7. The method of claim 1, wherein conducting a bending performance detection to the flexible screen comprises:

detecting a mechanical reliability of the flexible screen after conducting the mechanical extrusion test to the flexible screen.

8. The method of claim 1, wherein conducting a bending performance detection to the flexible screen comprises:

detecting an optical reliability and/or electrical reliability of the flexible screen at the time of/after conducting the mechanical extrusion test to the flexible screen.

9. A system for bending test of a flexible screen, comprising:

a mounting device, configured to connected with the flexible screen, the mounting device adapted to fasten the flexible screen in a relative flexible manner using an elastic material so that the mounting device is deformed when the flexible screen is extruded;

an extrusion device, configured to conduct a mechanical extrusion test to the flexible screen to bend the flexible screen by placing an extrusion point for the mechanical extrusion test away from connection points between the flexible screen and the mounting device; and a detection device, configured to conduct a bending performance detection to the flexible screen, wherein the extrusion device includes an extrusion head in a shape of sphere with a smoothly curved surface, wherein the mounting device further comprises a regulating device, and the extrusion head is regulated by the regulating device of the mounting device so that different positions of the extrusion point are selected in each test, and wherein the mechanical extrusion test is repeated up to multiple times in a preset time.

10. The system of claim 9, wherein the mounting device is adapted to be connected to opposite ends of the flexible screen; the extrusion device is adapted to approach the flexible screen, and extrude the flexible screen so that the degree of bending of the flexible screen is gradually increased.

11. The system of claim 9, wherein the mounting device comprises a fixing support, and a mounting component provided on the fixing support and configured to fix the flexible screen.

12. The system of claim 11, wherein the mounting component is made of an elastic material and is adapted to be deformed and stretched when the flexible screen is extruded.

13. The system of claim 11, wherein the extrusion device comprises an extrusion component and a drive;

the extrusion component comprises a connecting rod connected with the extrusion head; and the drive is fixed on the fixing support, the connecting rod is connected to the extrusion head, and the extrusion head is driven to conduct the mechanical extrusion test to the flexible screen.

14. The system of claim 13, wherein the regulating device is provided on the fixing support and adapted to move with respect to the fixing support, the drive being connected to the fixing support via the regulating device.

15. The system of claim 13, wherein the connecting rod is coupled to the extrusion head in a threaded connection.

* * * * *